(12) United States Patent
Dwivedi et al.

(10) Patent No.: US 9,879,011 B2
(45) Date of Patent: Jan. 30, 2018

(54) AMORPHOUS FORM OF LINAGLIPTIN AND PROCESS FOR PREPARATION THEREOF

(71) Applicant: CADILA HEALTHCARE LIMITED, Gujarat (IN)

(72) Inventors: Shriprakash Dhar Dwivedi, Gujarat (IN); Ashok Prasad, Gujarat (IN); Kuldeep Natwarlal Jain, Gujarat (IN); Kumar Kamlesh Singh, Gujarat (IN); Jitendra Maganbhai Gajera, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 84 days.

(21) Appl. No.: 14/384,567

(22) PCT Filed: Mar. 12, 2013

(86) PCT No.: PCT/IN2013/000148
§ 371 (c)(1),
(2) Date: Sep. 11, 2014

(87) PCT Pub. No.: WO2013/171756
PCT Pub. Date: Nov. 21, 2013

(65) Prior Publication Data
US 2015/0051228 A1 Feb. 19, 2015

(30) Foreign Application Priority Data
Mar. 12, 2012 (IN) .......................... 653/MUM/2012

(51) Int. Cl.
*C07D 473/04* (2006.01)
*C07D 473/06* (2006.01)

(52) U.S. Cl.
CPC ......... *C07D 473/04* (2013.01); *C07D 473/06* (2013.01); *Y10T 428/2982* (2015.01)

(58) Field of Classification Search
None
See application file for complete search history.

(56) References Cited

U.S. PATENT DOCUMENTS

2013/0123282 A1* 5/2013 Metsger ............... C07D 473/04
514/263.21

FOREIGN PATENT DOCUMENTS

| WO | WO 2004/018468 A2 | 3/2004 |
| WO | WO 2006/048427 A1 | 5/2006 |
| WO | WO 2007/128721 A1 | 11/2007 |
| WO | WO 2013/074817 A1 | 5/2013 |

OTHER PUBLICATIONS

CAPLUS printout of Patent No. IP210079D, published on Aug. 25, 2011.*
Anon.: "Process for Preparing an Amorphous Form of 8-[3(R)-Amino-1-piperidinyl]-7-(2-butynyl)-3-methyl-1-(4-methyl-2-quinazolinylmethyl)xanthine", ip.com Journal, 11(9A), 22 (No. IPCOM000210079D, vol. 11(9A), No. 22, Aug. 25, 2011, X5002713354.
Anon.: "A process for Preparing an Amorphous Form of 8-[3(R)-arninopiperidin-1-yl]-7-(2-butynyl)-3-methyl-1-(4-methylquinazolin-2ylmethyl)Xanthine". ip.com Journal, 12(7B), 14 (No. IPCOM00219543D), vol. 12(7B), No. 14, Jul. 5, 2012. X5002713355.
Petit S., et al.: "The Amorphous State", Jan. 1, 2006, Jan. 1, 2006, pp. 259-285, XP002481458.

* cited by examiner

*Primary Examiner* — Alicia L Otton
*Assistant Examiner* — Po-Chih Chen
(74) *Attorney, Agent, or Firm* — Ladas & Parry LLP (57) ABSTRACT

The present invention relates to an amorphous form of linagliptin and processes for the preparation thereof. The invention also relates to a pharmaceutical composition comprising a therapeutically effective amount of an amorphous form of linagliptin and use of the composition for treatment of diabetes especially type-I or type-II, prediabetes or reduction of glucose tolerance.

22 Claims, 2 Drawing Sheets

AMORPHOUS FORM OF LINAGLIPTIN AND PROCESS FOR PREPARATION THEREOF

This application is a 371 of International Patent Application No. PCT/IN2013/000148filed 12 Mar. 2013, which claimed priority to India Patent Application No. 653/MUM/2012filed 12 Mar. 2012.

FIELD OF THE INVENTION

The invention relates to an amorphous form of linagliptin. More particularly, it relates to processes for the preparation of an amorphous form of linagliptin. The invention also relates to a pharmaceutical composition comprising therapeutically effective amount of an amorphous form of linagliptin and use of said composition for treatment of diabetes especially type-I or type-II, prediabetes or reduction of glucose tolerance.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Linagliptin i.e. 8-[(R)-3-aminopiperidin-1-yl]-7-(but-2-yn-1-yl)-3-methyl-1-[(4-methyl-quinazolin-2-yl)methyl]-3,7-dihydro-1H-purine-2,6-dione of Formula (1) or salts thereof is disclosed in U.S. Pat. No. 7,407,955 B2 and the process by which it can be prepared.

(1)

U.S. Pat. No. 7,820,815 B2 discloses an alternative process for preparing linagliptin using (R)-3-phthalimidopiperidine tartrate as an intermediate.

U.S. Patent Application Publication No. 2007/0259900 A1 (the US '900 A1) discloses five crystalline forms of linagliptin namely Form-A, Form-B, Form-C, Form-D and Form-E. The US '900 A1 also discloses that the compound prepared in WO 2004/018468 A2 is present at ambient temperature as a mixture of two enantiotropic polymorphs. The temperature at which the two polymorphs transform into one another is 25±15° C.

The US '900 A1 discloses that pure high temperature form (polymorph A) can be obtained by heating the mixture to temperatures >40° C. and its melts at 206±3° C. and is characterized by x-ray powder diagram and d-values. Further US '900 A1 also discloses that the low temperature (polymorph B) is obtained by cooling to temperatures <10° C.

According to the European Medicines Agency Assessment Report for Trajenta (linagliptin), the active substance is a white to yellowish crystalline solid substance and simultaneously exists in two polymorphic forms, which are enantiotropically related and which reversibly convert into each other approximately at room temperature. The two polymorphic forms do not differ with regard to biopharmaceutical properties.

IP.COM Journal Vol. 12 (4A) Pg. 15 (2011) i.e. IPCOM000210079D discloses a process for preparing an amorphous form of 8-[(R)-3-aminopiperidin-1-yl]-7-(but-2-yn-1-yl)-3-methyl-1-[(4-methyl-quinazolin-2-yl)methyl] xanthine i.e. linagliptin by dissolving linagliptin in dichloromethane and evaporating under reduced pressure to afford dry solid residue which was amorphous by XRD. This process has the drawback of removal of residual solvent. The dichloromethane is difficult to remove from amorphous linagliptin even upon prolonged drying.

Another example provided discloses a process for preparing an amorphous form of linagliptin by mixing linagliptin in ethanol to get partial dissolution followed by evaporation under reduced pressure to obtain dry solid residue. This solid residue was reported to be amorphous. The said process may not be suitable for industrial application as the residue obtained has higher amount of residual ethanol.

IP.COM Journal Vol. 12 (4A) Pg. 15 (2012) i.e. IPCOM000216218D published after the priority date of this application discloses process for preparation of amorphous 8-[(R)-3-aminopiperidin-1-yl]-7-(but-2-yn-1-yl)-3-methyl-1-[(4-methyl-quinazolin-2-yl)methyl]xanthine hydrochloride i.e. linagliptin hydrochloride which is cited herein as reference.

The processes disclosed in the prior art doesn't provide amorphous linagliptin which is suitable in use for pharmaceutical developments. The prior art provides amorphous linagliptin which is having higher amount of residual solvents and the processes not applicable for commercial manufacturing.

U.S. Patent Application Publication No. 2010/0209506 A1 discloses a pharmaceutical composition comprising linagliptin as a first active pharmaceutical ingredient and a glucopyranosyl-substituted benzene derivative as second active pharmaceutical ingredient wherein the linagliptin has a particle size distribution of d90<200 µm.

Therefore, there is a need to provide a process for the preparation of amorphous linagliptin which is substantially free from residual solvent and the processes are industrially scalable for bulk manufacturing. Further, the process provides an amorphous form of linagliptin which is at least stable at ordinary storage conditions during stability.

Crystalline solids normally require a significant amount of energy for dissolution due to their highly organized, lattice like structures. For example, the energy required for a drug molecule to escape from a crystal is more than from an amorphous or a non-crystalline form. It is known that the amorphous forms in a number of drugs exhibit different dissolution characteristics and in some cases different bioavailability patterns compared to the crystalline form (Econno T., Chem. Pharm. Bull., 1990; 38: 2003-2007). For some therapeutic indications, one bioavailability pattern may be favoured over another.

An amorphous form of some of the drugs exhibit much higher bioavailability than the crystalline forms, which leads to the selection of the amorphous form as the final drug substance for pharmaceutical dosage from development. Additionally, the aqueous solubility of crystalline form is lower than its amorphous form in some of the drugs, which may result in the difference in their in vivo bioavailability. Therefore, it is desirable to have amorphous forms of drugs with high purity to meet the needs of regulatory agencies and also highly reproducible processes for their preparation.

In view of the above, it is therefore, desirable to provide an efficient, economical and eco-friendly process for the preparation of stable amorphous form of linagliptin.

SUMMARY OF THE INVENTION

Accordingly, the invention provides a storage stable amorphous form of linagliptin of Formula (1).

In one embodiment, there is provided an improved process for the preparation of amorphous form of linagliptin.

In another embodiment, there is provided amorphous form of linagliptin having water content less than 0.5% wt/wt.

In another embodiment, there is provided an improved process for preparation of an amorphous form of linagliptin, the process comprising:
a) providing a solution of linagliptin in a suitable solvent or mixture of solvents; and
b) obtaining the amorphous form of linagliptin by removal of solvent.

In another general aspect, there is provided an improved process for preparation of an amorphous form of linagliptin, the process comprising:
(a) suspending linagliptin in a suitable organic solvent and removing the solvent to obtain residue;
(b) adding suitable anti-solvent to the residue; and
(c) obtaining an amorphous form of linagliptin.

In another embodiment, there is provided an improved process for preparation of an amorphous form of linagliptin, the process comprising:
(a) reacting (R)-tert-butyl 1-(7-(but-2-ynyl)-3-methyl-1-((4-methylquinazolin-2-yl)methyl)-2,6-dioxo-2,3,6,7-tetrahydro-1H-purin-8-yl)piperidin-3-ylcarbamate of Formula (2) with an acid in a first organic solvent to obtain reaction mixture;
(b) basifying the reaction mixture with a base thereby separating organic layer;
(c) acidifying the separated organic layer with suitable acid followed by treatment with a base to adjust the basic pH;
(d) removing the first organic solvent to obtain residue;
(e) treating the residue with second organic solvent followed by its partial removal to obtain linagliptin;
(f) dissolving linagliptin in the first organic solvent and removing the solvent to obtain residue; and
(g) obtaining an amorphous form of linagliptin by treating the residue with suitable anti-solvent.

In yet another embodiment there is provided an amorphous form of linagliptin substantially free from residual organic solvents.

In still another embodiment, there is provided storage and packaging conditions for amorphous form of linagliptin.

Figure 1:
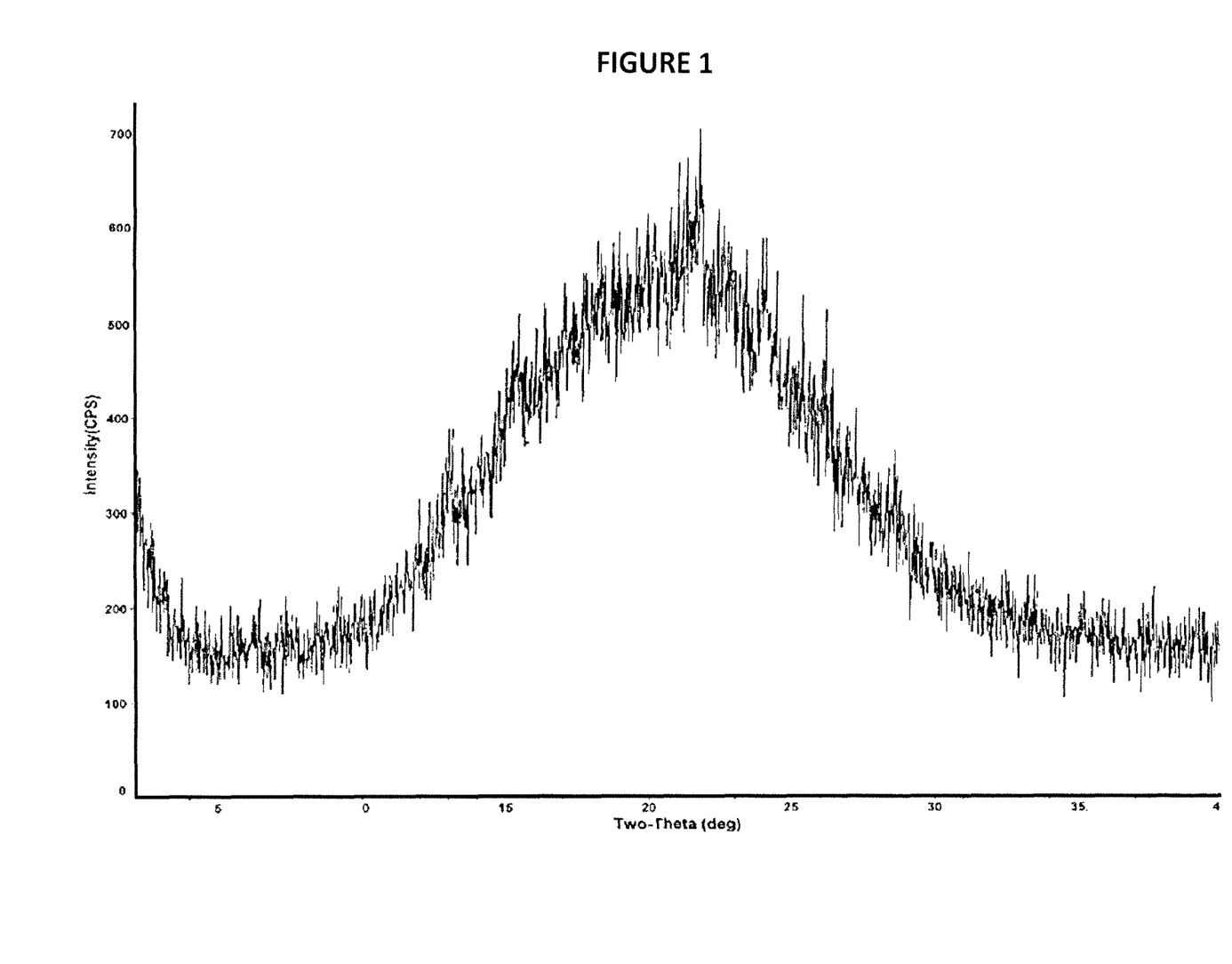
FIG. 1: Shows X-ray diffractogram (XRD) of amorphous form of linagliptin as in Example-1.
Figure 2:
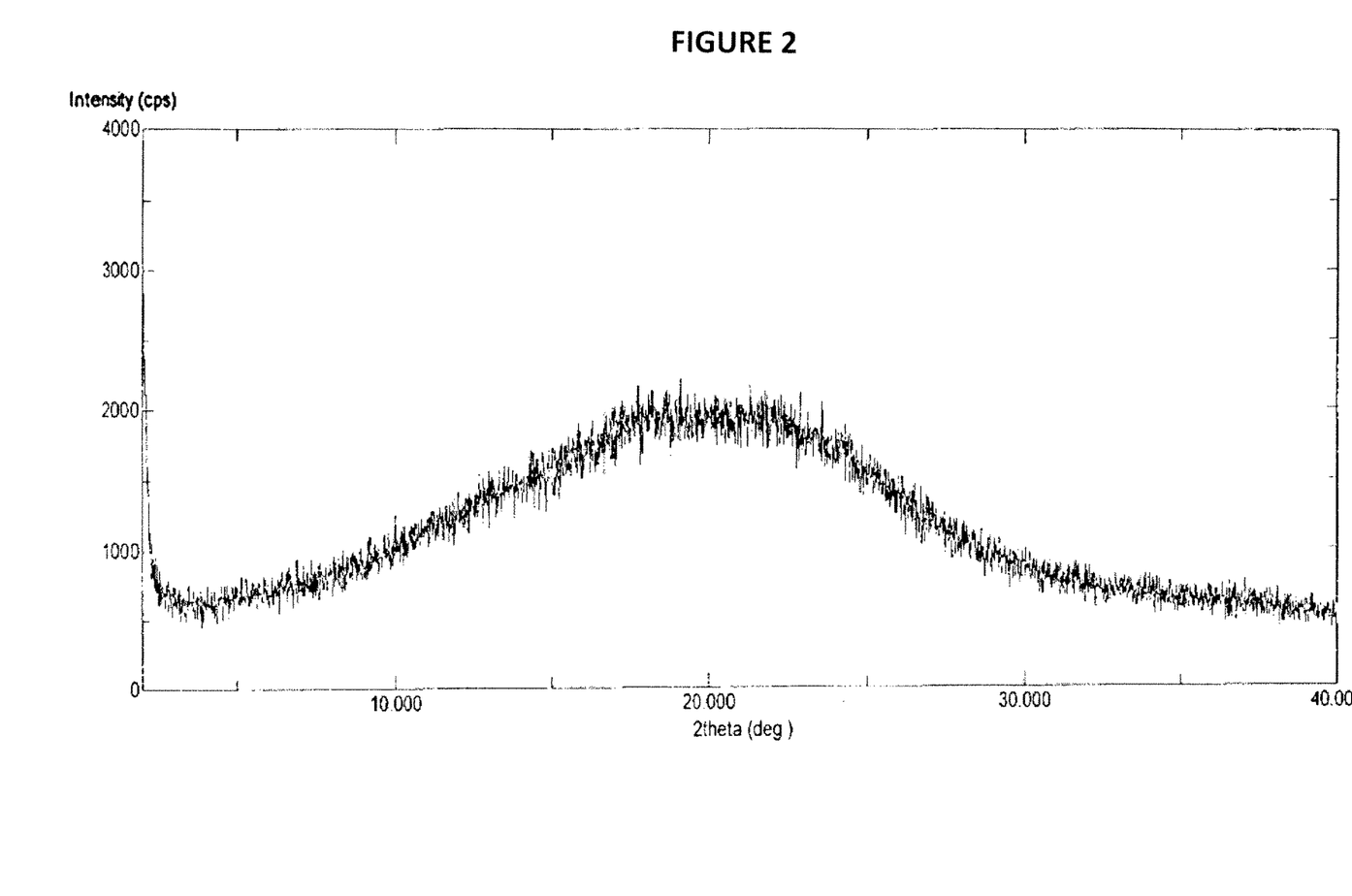
FIG. 2: Shows X-ray diffractogram (XRD) of amorphous form of linagliptin as in Example-7.

In another embodiment, amorphous form of linagliptin is characterized by X-ray powder diffraction as depicted in FIG. 1 and FIG. 2.

In another embodiment, there is provided particle size of the amorphous form of linagliptin.

The amorphous form of linagliptin having particle size distributions wherein the 10th volume percentile particle size (D10) is less than about 50 µm, the 50th volume percentile particle size (D50) is less than about 200 µm, or the 90th volume percentile particle size (D90) is less than about 400 µm, or any combination thereof.

In another aspect there is provided an amorphous form of linagliptin having particle size in terms of D95, preferably less than about 100 microns, more preferably less than about 50 microns and most preferably less than about 30 microns.

In another aspect there is provided an amorphous form of linagliptin having particle size in terms of D95 less than about 100 microns.

In another general aspect, there is provided an amorphous form of linagliptin of Formula (I) having purity greater than about 95%, or greater than about 98%, or greater than about 99%, or greater than about 99.5%, or greater than about 99.8%, or greater than about 99.9%, as determined by using high performance liquid chromatography (HPLC).

In another embodiment, there is provided a pharmaceutical composition comprising therapeutically effective amount of an amorphous form of linagliptin substantially free from residual solvents together with pharmaceutically acceptable excipients, carrier and diluents.

In another embodiment, there is provided a pharmaceutical composition comprising the therapeutically effective amount of stable amorphous form of linagliptin together with one or more pharmaceutically acceptable carriers, excipients or diluents.

In another embodiment; there is a pharmaceutical composition comprising a therapeutically effective amount of an amorphous form of linagliptin together with one or more pharmaceutically acceptable carriers, excipients or diluents and use thereof for the treatment of diabetes especially type-I or type-II or prediabetes or reduction of glucose tolerance.

DETAILED DESCRIPTION OF THE INVENTION

As used herein, the terms "suspending", "slurrying" and "triturating" are interchangeable, and refer to a process carried out in a heterogeneous mixture where complete dissolution does not occur. Also, heating the suspension or slurry can result in a homogenous mixture where complete or partial dissolution occurs at an elevated temperature or ambient temperature.

The term "elevated temperature" used herein means, heating the reaction mixture either heterogeneous or homogeneous at a temperature from about 35° C. to boiling point of solvent, in particular, from about 35° C. to about 100° C. The term "ambient temperature" used herein means, the temperature from about 0° C. to about 35° C. of solvent.

As used herein, the terms "obtaining" means isolating the amorphous form of linagliptin by way of filtration, filtration under vacuum, centrifugation, decantation, evaporation, evaporation under reduced pressure, distillation and the like. The product obtained may be further or additionally dried to achieve the desired moisture values. For example, the product may be dried in a tray drier, dried under vacuum and/or in a Fluid Bed Drier.

As used herein, "storage stable" includes the amorphous form of linagliptin after exposure to a relative humidity of 75% at 40° C. or relative humidity of 60% at 25° C., for a period of at least three months shows no change in polymorphic form by x-ray powder diffraction.

"Suitable solvent" means a single or a combination of two or more solvents.

As used throughout the disclosure, the term D95 means that 95% of the particles (based on volume) are smaller than or equal to the indicated size.

As used herein "substantially free" includes amorphous linagliptin having residual organic solvents well within the limits of ICH guidelines as per chapter Q3C.

In one general aspect, there is provided a storage stable amorphous form of linagliptin of Formula (1)

(1)

In another embodiment, there is provided a process for the preparation of an amorphous form of linagliptin without simultaneous formation of crystalline forms or which will enable the conversion of crystalline forms into an amorphous form.

In another embodiment, there is provided an amorphous form of linagliptin having water content less than 0.5% wt/wt.

In another embodiment, there is provided an improved process for preparation of an amorphous form of linagliptin, the process comprising:
a) providing a solution of linagliptin in a suitable solvent or mixture of solvents;
b) obtaining the amorphous form of linagliptin by removal of solvent.

The suitable solvent comprises water; alcohols such as methanol, ethanol, isopropanol and the like; ketones such as acetone, butanone and the like; esters such as ethyl acetate, butyl acetate and the like; halogenated hydrocarbons like methylene dichloride, ethylene dichloride, chlorobenzene, and the like, nitriles like acetonitrile; polar aprotic solvents like dimethylformamide, dimethylacetamide, N-methylpyrrolidone, dimethyl-sulfoxide, tetrahydrofuran or mixtures thereof. In particular, mixture of tetrahydrofuran and methanol may be used.

The embodiments of the process involve obtaining an amorphous form of linagliptin by removal of solvent. The isolation of amorphous form may be affected by removing the solvent. The suitable techniques which may be used for the removal of solvent include using a rotational distillation device like a Buchi Rotavapor, spray drying, agitated thin film drying ("ATFD"), freeze drying (lyophilization), and the like or any other suitable technique.

A preferred embodiment of the invention includes spray drying a solution of linagliptin. It involves the spray drying of feed stock, which is prepared as discussed below. The feedstock is dozed into the spray-drying instrument JISL Mini Spray-drier LSD-48 and spray drying is carried out under the following parameters.

| Sr. No | Parameters | Conditions |
|---|---|---|
| a) | Feed pump | 10-50 rpm |
| b) | Inlet temperature | 35°-80° C. |
| c) | Outlet temperature | 30°-60° C. |
| d) | Aspirator rate | 1000-1500 rpm |
| e) | Vacuum for conveying the dry product | 30-120 mm of Hg |
| f) | Hot air supply | 2-4 Kg/cm$^2$ |
| g) | Atomizer Speed: | 40,000-100,000 rpm |

The feedstock for spray drying is either a clear solution or in dispersion form.

In another embodiment, the spray drying of linagliptin is performed by a) maintaining the feed rate of the feed stock at 50-250 mL/hr, particularly 100-200 mL/hr; b) maintaining the inlet temperature in the range of 35° C.-80° C., particularly, 50° C.-70° C.; c) maintaining the aspirator rate between 1000-1500 rpm, particularly 1200-1400 rpm; d) maintaining the outlet temperature in the range of 30° C. to 60° C., particularly, 40° C. to 50° C.; e) maintaining air flow at 2-4 Kg/cm, particularly 2 Kg/cm; f) maintaining atomizer speed between 20,000-100,000 rpm, particularly, 40,000-50,000 rpm, and; g) maintaining the vacuum at 30-120 mm of Hg, particularly 50-80 mm of Hg.

The feed stock of linagliptin may be conveniently prepared by dissolving linagliptin in a suitable solvent comprises one or more of methanol, ethanol, ethyl acetate, acetonitrile, methylene dichloride, tetrahydrofuran, water or mixture thereof. In particular, water, methanol, ethanol, acetone, ethyl acetate, methylene dichloride, water-methanol or water-ethanol, water-acetone, methanol-tetrahydrofuran are suitable solvent used or such solvents that evaporate easily to afford dry product, most particularly methanol, ethanol, methylene dichloride, tetrahydrofuran or mixtures of the above may be used.

In another embodiment, there is provided an improved process for the preparation of an amorphous form of linagliptin, the process comprising:
a) suspending linagliptin in a suitable organic solvent and removing the solvent to obtain residue;
b) adding suitable anti-solvent to the residue; and
c) obtaining the amorphous form of linagliptin.

The suspension in step a) may be obtained by the known methods that include:
(i) direct use of a reaction mixture containing linagliptin that is obtained in the course of its synthesis; or
(ii) suspending linagliptin in a suitable solvent or mixture of solvents.

The suitable solvent comprises one or more of water; alcohols like methanol, ethanol, isopropanol, n-butanol, t-butyl alcohol, and the like; ketones like acetone, butanone, methyl butyl ketone, methyl isobutyl ketone, and the like; esters like ethyl acetate, isopropyl acetate, t-butyl acetate, and the like; chlorinated hydrocarbons like methylene dichloride, ethylene dichloride, chlorobenzene, and the like, nitriles like acetonitrile, polar aprotic solvents like dimethylformamide, dimethylacetamide, N-methylpyrrolidone, dimethyl-sulfoxide, and mixtures thereof. In particular, methylene dichloride may be used.

The embodiment of the process comprises removal of the solvent from the suspension of linagliptin. The solvent may be removed by suitable techniques which may be used for the removal of solvent include using a rotational distillation device like a Buchi Rotavapor, distillation under vacuum, evaporation, evaporation under reduced pressure, decantation, filtration and any other suitable techniques applicable.

The suitable anti-solvent comprises one or more of hexanes, n-heptane, n-pentane, cyclohexane, methylcyclohexane and the like; aromatic hydrocarbons like toluene, xylene, ethylbenzene and the like; ethers like diethyl ether, diisopropyl ether, methyltert-butyl ether, dibutyl ether, tetrahydrofuran, 1,4-dioxane, 2-methoxyethanol and the like. In particular, methyl tert-butyl ether may be used.

The step c) involves obtaining an amorphous form of linagliptin. The isolation may be affected by removing the solvent. Suitable techniques, which may be used for the removal of solvent comprises one or more as disclosed herein above.

In another embodiment, there is provided an improved process for preparation of an amorphous form of linagliptin, the process comprising:
(a) reacting (R)-tert-butyl 1-(7-(but-2-ynyl)-3-methyl-1-((4-methylquinazolin-2-yl)methyl)-2,6-dioxo-2,3,6,7-tetrahydro-1H-purin-8-yl)piperidin-3-ylcarbamate of Formula (2) with an acid in a first organic solvent to obtain reaction mixture;
(b) basifying the reaction mixture with a base thereby separating organic layer;
(c) acidifying the separated organic layer with suitable acid followed by treatment with a base to adjust the basic pH;
(d) removing the first organic solvent to obtain residue;
(e) treating the residue with a second organic solvent followed by its partial removal to obtain linagliptin;
(f) dissolving linagliptin in the first organic solvent and removing the solvent to obtain residue; and
(g) obtaining an amorphous form of linagliptin by treating the residue with suitable anti-solvent.

The starting compound (R)-tert-butyl 1-(7-(but-2-ynyl)-3-methyl-1-((4-methylquinazolin-2-yl)methyl)-2,6-dioxo-2,3,6,7-tetrahydro-1H-purin-8-yl)piperidin-3-ylcarbamate of Formula (2) may be prepared by the known process disclosed in the prior art for example U.S. Pat. No. 7,407,955 B2 which is incorporated herein as reference in its entirety.

(2)

The first organic solvent comprises one or more of water, methanol, ethanol, isopropanol, ethyl acetate, isopropyl acetate, methylene dichloride, dimethylformamide, dimethylsulfoxide, tetrahydrofuran and the like. In particular, methylene dichloride may be used.

The acid used in step (a) comprises one or more of hydrochloric acid, sulfuric acid, acetic acid, triflouroacetic acid, formic acid, hydrobromic acid and the like. In particular, hydrochloric acid or triflouroacetic acid may be used to obtain reaction mixture.

The reaction mixture thus obtained may be basified with an aqueous base. The aqueous base comprises solution of suitable base in water. The suitable base comprises sodium carbonate, potassium carbonate, sodium bicarbonate, potassium bicarbonate, sodium hydroxide, potassium hydroxide, lithium hydroxide and the like. In particular potassium bicarbonate may be used.

The embodiment of the process comprises preparing aqueous solution of potassium bicarbonate in water and adding the solution to the reaction mixture in step (a). The reaction mixture may be stirred for 10 minutes to 5 hours thereby separating the aqueous and organic layer.

The separated organic layer may be acidified with suitable acid. The suitable acid comprises one or more of oxalic acid, tartaric acid, succinic acid, acetic acid, citric acid, phthalic acid, methane sulfonic acid, toluene sulfonic acid, mandelic acid or their aqueous solutions to obtain acid addition salt in reaction mixture. In particular oxalic acid solution in water may be added to obtain oxalate salt, which is not isolated.

The separated aqueous layer may be basified with suitable base in presence of first organic solvent. The suitable base comprises sodium carbonate, potassium carbonate, sodium bicarbonate, potassium bicarbonate, sodium hydroxide, potassium hydroxide, lithium hydroxide and the like. In particular sodium hydroxide may be used to adjust the basic pH. In particular, the pH of about 8-9 may be adjusted by addition of base.

The embodiment of the process comprises removing the first organic solvent to obtain residue. The solvent may be removed by distillation under atmospheric pressure at 40° C. to 45° C. The residue thus obtained was treated with second organic solvent.

The second organic solvent comprises one or more of methanol, ethanol, isopropanol, acetone, methyl ethyl ketone, methyl isobutyl ketone, toluene, xylene, hexane, heptane, cyclohexane, diisopropyl ether, diethyl ether, methyl tert-butyl ether and the like. In particular, isopropanol may be used.

The suspension of linagliptin in isopropanol may be distilled till partial removal of isopropanol by distillation under vacuum at 50° C. to 55° C. The reaction mixture may be cooled to 0° C. and filtered. The obtained linagliptin may be washed with methyl tertbutyl ether.

The embodiment of the process further comprises dissolving the obtained linagliptin in first organic solvent and removing the solvent to obtain residue. The residue was treated with suitable anti-solvent to obtain an amorphous form of linagliptin.

The suitable anti-solvent comprises one or more of hexanes, n-heptane, n-pentane, cyclohexane, methylcyclohexane and the like; aromatic hydrocarbons like toluene, xylene, ethylbenzene and the like; ethers like diethyl ether, diisopropyl ether, t-butyl methyl ether, dibutyl ether, 1,4-dioxane, 2-methoxyethanol and the like. In particular, methyl tert-butyl ether may be used. In particular, methyl tert-butyl ether may be used.

The obtained linagliptin may be dried under vacuum at about 50° C. to 70° C. for 6-12 hours to get amorphous form substantially free from residual solvents. Thus obtained amorphous linagliptin is stable under ordinary stability conditions at least for 3 months and doesn't change to crystalline form.

In another embodiment, there is provided an amorphous form of linagliptin substantially free from residual organic solvents.

In another embodiment, there is provided storage and packaging conditions for amorphous form of linagliptin.

The stable amorphous form of linagliptin may be stored under nitrogen atmosphere and packed in a double polythene bag tied with a thread, keeping primary packing containing amorphous linagliptin inside a black color polyethylene bag containing oxygen busters and sealing it, placing above the double polyethylene bag inside a triple laminated bag optionally containing oxygen busters and sealing it, and placing the sealed triple laminated bag inside a closed high density polyethylene (HDPE) container and storing in controlled environment chamber at about 25° C. and/or 40° C.

In another general aspect, the amorphous form of linagliptin is characterized by X-ray powder diffraction as depicted in FIG. 1 and FIG. 2

In another embodiment, there is provided an improved process for the preparation of an amorphous form of linagliptin, substantially free from residual organic solvents, the process comprising:
(a) providing linagliptin having less than 10% residual organic solvent;
(b) triturating linagliptin in methyl tert-butyl ether, or contacting linagliptin with humid air in a fluidized bed drier, or drying linagliptin under reduced pressure of less than about 30 mmHg at less than 60° C.;
(c) optionally micronizing linagliptin; and
(d) drying the product obtain in step c) to obtain amorphous form of linagliptin substantially free of residual organic solvents.

In another embodiment, the invention provides an amorphous form of linagliptin having particle size distributions wherein the 10th volume percentile particle size (D10) is less than about 50 µm, the 50th volume percentile particle size (D50) is less than about 20.0 µm, or the 90th volume percentile particle size (D90) is less than about 400 µm, or any combination thereof.

In another embodiment there is provided an amorphous form of linagliptin having particle size in terms of D95, is preferably less than about 100 microns, more preferably less than about 50 microns and most preferably less than about 30 microns.

In another embodiment, there is provided a process for preparing amorphous linagliptin having particle size in terms of D95 less than about 100 microns, comprising the steps of;
(a) milling amorphous linagliptin,
(b) slurrying the milled linagliptin in one or more organic solvents to form a solution; and
(c) obtaining the amorphous form of linagliptin having particle size in terms of D95 less than about 100 microns by removal of solvent.

The milling of linagliptin in step (a) may be performed with feeding pressure of about 3 kg and grinding pressure of about 4 kg. The suitable solvent for step (b) comprises one or more of $C_{3-6}$ ketones like acetone, water, N-methylpyrrolidone, $C_{3-6}$ amides like dimethylformamide, dimethylacetamide, halo-substituted $C_{6-12}$ aromatic hydrocarbons like chlorobenzene, dimethylsulfoxide, dimethylcarbonate, $C_{1-8}$ alkyl alcohols like methanol, ethanol, acetonitrile, $C_{2-6}$ alkyl acetates like ethyl acetate, isopropyl acetate, cellosolve, and $C_{2-8}$ ethers like methyl tert-butyl ether.

In another embodiment, the present invention provides an amorphous form of linagliptin of Formula (I) having purity greater than about 90%, or greater than about 95%, or greater than about 98%, or greater than about 99%, or greater than about 99.5%, or greater than about 99.8%, or greater than about 99.9%, as determined using high performance liquid chromatography (HPLC).

Powder X-ray Diffraction of an amorphous form of linagliptin can be obtained under following conditions
(i) Characterization by Powder X-ray Diffraction The X-ray powder diffraction spectrum was measured under the following experimental conditions:
Instrument: X-Ray Diffractometer, D/Max-2200/PC Make: Rigaku, Japan.
X-Ray: Cu/40 kv/40 mA
Diverging: 10
Scattering Slit: 10
Receiving Slit: 0.15 mm
Monochromator RS: 0.8 mm
Counter: Scintillation Counter
Scan Mode: Continuous
Scan Speed: 3.0000/Min
Sampling Width: 0.020
Scan Axes: Two Theta/Theta
Scan Range: 2.0000 to 40.0000
Theta Offset: 0.0000

In another embodiment, linagliptin to be used as the starting material may be prepared by the known methods reported in the prior art i.e. by using the process as per U.S. Pat. No. 7,407,955 B2.

In another embodiment, there is provided a pharmaceutical composition comprising therapeutically effective amount of an amorphous form of linagliptin substantially free from residual solvents together with pharmaceutically acceptable excipients, carrier and diluents.

In another embodiment, there is provided a pharmaceutical composition comprising the therapeutically effective amount of stable amorphous form of linagliptin together with one or more pharmaceutically acceptable excipients, carrier and diluents.

In another embodiment, there is provided a pharmaceutical composition comprising a therapeutically effective amount of amorphous linagliptin substantially free from crystalline form, and one or more pharmaceutically acceptable carriers, excipients or diluents.

In another embodiment, there is a pharmaceutical composition comprising a therapeutically effective amount of an amorphous form of linagliptin together with one or more pharmaceutically acceptable carriers, excipients or diluents and use thereof for the treatment of diabetes especially type-I or type-II or prediabetes or reduction of glucose tolerance.

The invention also encompasses pharmaceutical compositions comprising linagliptin or salts thereof of the invention. As used herein, the term "pharmaceutical compositions" includes tablets, pills, powders, liquids, suspensions, emulsions, granules, capsules, suppositories, or injection preparations.

Pharmaceutical compositions containing the linagliptin of the invention may be prepared by using diluents or excipients such as fillers, bulking agents, binders, wetting agents, disintegrating agents, surface active agents, and lubricants. Various modes of administration of the pharmaceutical compositions of the invention may be selected depending on the therapeutic purpose, for example tablets, pills, powders, liquids, suspensions, emulsions, granules, capsules, suppositories, or injection preparations.

Having described the invention with reference to certain preferred embodiments, other embodiments will become apparent to one skilled in the art from consideration of the specification. The process for preparation of the amorphous form of linagliptin is demonstrated in examples illustrated below. These examples are provided as illustration only and therefore should not be construed as limitation of the scope of invention.

EXAMPLE-1

Preparation of Amorphous Form of Linagliptin 25.0 g of linagliptin is dissolved in 250.0 mL of THF-methanol mixture at 25° C. to 30° C. The content is stirred for 30 minutes at 25° C. to 30° C. To this, 1.0 g charcoal was added and stirred for 30 minutes at 25° C. to 30° C. The content is filtered through Hyflosupercel, and the Hyflosupercel pad is washed with 50.0 mL methanol. The filtrate is concentrated under vacuum below 45° C. followed by spray drying in JISL Mini spray drier LSD-48 under the below conditions. The product is collected from cyclone and is further dried at 40° C.±5° C. under vacuum for 12 hours to get 19.0 g of amorphous linagliptin.

| Sr. No | Parameters | Conditions |
|--------|------------|------------|
| a) | Feed pump | 30 rpm |
| b) | Inlet temperature | 60° C. |
| c) | Outlet temperature | 40° C. |
| d) | Aspirator rate | 1300 rpm |
| e) | Vacuum for conveying the dry product | 80 mm of Hg |
| h) | Hot air supply | 2 Kg/cm² |

The spray-dried linagliptin is amorphous in nature. The obtained product contains residual solvent well within ICH limit. The obtained solid was amorphous linagliptin as is shown by the x-ray diffraction pattern shown in FIG. 1.

EXAMPLE-2

Preparation of the Amorphous Form of Linagliptin 10 g of linagliptin was dissolved in 125 mL methanol and heated to obtain clear solution at 65° C. To this stirred solution was slowly added 100 ml acetone at room temperature, and stirred for an additional 2-3 hours. The resulting suspension was filtered and dried in air. The obtained solid was amorphous linagliptin having x-ray diffraction pattern shown in FIG. 1.

EXAMPLE-3

Preparation of the Amorphous Form of Linagliptin 10 g of linagliptin was dissolved in 125 mL methylene dichloride and heated to obtain clear solution at 50° C. The reaction mixture was distilled atmospherically at 40-45° C. 100 mL isopropanol was added to the residue and stirred for 15 minutes. The reaction mixture was distilled partially and filtered. The wet-cake was dissolved in 125 mL methylene dichloride. The solution was distilled to remove methylene dichloride and the residue was triturated with 75 mL methyltert-butyl ether at 0° C. The precipitated product was filtered and washed with methyltert-butyl ether. The product was dried under vacuum at 60° C. for 6 hours to obtain amorphous linagliptin having x-ray diffraction pattern shown in FIG. 2.

EXAMPLE-4

Preparation of the Amorphous Form of Linagliptin 10 g of amorphous linagliptin having residual content of about 10% was dried in fluid bed dried at 45° C. for 2 days to obtain amorphous linagliptin having water content less than 0.5% wt/wt and residual content within the ICH limits. The obtained amorphous linagliptin was characterized by x-ray diffraction pattern.

EXAMPLE-5

Preparation of the Amorphous Form of Linagliptin 10 g of linagliptin having residual organic solvent of about 10% was dried in vacuum tray dryer at about 5 to about 60° C., under pressure of less than 30 mm/Hg for a period of 24 hours to obtain amorphous linagliptin having residual organic solvent well within ICH limit. The obtained amorphous form of linagliptin was characterized by x-ray diffraction pattern.

EXAMPLE-6

Preparation of the Amorphous Form of Linagliptin 10 g of linagliptin having residual organic solvent of about 10% was dried in vacuum tray dryer at about 5 to about 60° C., under pressure of less than 30 mm/Hg for a period of 24 hours to obtain amorphous linagliptin having residual organic solvent well within ICH limit. The obtained amorphous form of linagliptin was characterized by x-ray diffraction pattern.

EXAMPLE-7

Preparation of the Amorphous Form of Linagliptin 19 g compound (2) and 190 mL methylene dichloride were stirred at 25° C. in round bottom flask. 70.3 g triflouro acetic acid and 95 mL methylene dichloride were added to the reaction mixture and stirred for 2 hours. 76 g aqueous potassium carbonate solution was cooled at 10° C. and added to the reaction mixture. The reaction mixture was stirred for 30 min at 25° C. and settled to separate the organic layer. The organic layer was treated with 3.68 g oxalic acid aqueous solution and stirred. 190 mL methylene dichloride was added to the separated aqueous layer and cooled to 20° C. 10% sodium hydroxide solution was added to the reaction mixture thereby to adjust the pH of 8-9. The separated organic layer was dried over sodium sulfate and filtered. The filtrate was distilled to remove methylene dichloride atmospherically at 40-45° C. 152 mL isopropanol was added to the residue and partially removed by distillation under vacuum at 50-55° C. followed by cooling to 0-5° C. The reaction mixture was filtered and washed with methyl tert-butyl ether. The wet-cake was dissolved in 190 mL methylene dichloride and stirred for 30 min. The methylene dichloride was distilled under atmospheric pressure and degassed. The reaction mixture was cooled at ambient temperature and 76 mL methyl tert-butyl ether was added. The precipitated product was stirred for 30 min and filtered. The wet-cake was washed with methyl tert-butyl ether and dried under vacuum at 60° C. for 6 hours to obtain amorphous linagliptin characterized by x-ray powder diffraction as depicted in FIG. 2.

We claim:

1. An amorphous form of linagliptin characterized by X-ray powder diffraction as depicted in FIG. 1 or FIG. 2.

2. A storage stable amorphous form of linagliptin wherein the amorphous linagliptin does not convert into any other polymorphic form when stored at a temperature up to 40° C. and at a relative humidity of 25% to 75% up to three months or more; wherein the amorphous form of linagliptin is characterized by X-ray powder diffraction as depicted in FIG. 1 or FIG. 2.

3. An amorphous form of linagliptin according to claim 2, substantially free from one or more residual solvents.

4. The amorphous form of linagliptin according to claim 2, having particle size distributions wherein the 10th volume percentile particle size ($D_{10}$) is 50 μm or less, the 50th volume percentile particle size ($D_{50}$) is 200 μm or less, or the 90th volume percentile particle size ($D_{90}$) is 400 μm or less, or any combination thereof.

5. The amorphous form of linagliptin according to claim 2, having particle size in terms of $D_{95}$ of 100 μm or less.

6. A pharmaceutical composition comprising a therapeutically effective amount of an amorphous form of linagliptin substantially free from one or more of residual solvents according to claim 3, together with pharmaceutically acceptable excipients, carrier and diluents.

7. A pharmaceutical composition comprising a therapeutically effective amount of stable amorphous form of linagliptin according to claim 2, together with one or more pharmaceutically acceptable excipients, carrier and diluents.

8. A pharmaceutical composition comprising a therapeutically effective amount of amorphous linagliptin according to claim 2 substantially free from crystalline form, and one or more pharmaceutically acceptable carriers, excipients or diluents.

9. A process for the preparation of an amorphous form of linagliptin according to claim 1, the process comprising:
(a) providing a solution of linagliptin in one or more solvents; and
(b) obtaining the amorphous form of linagliptin by the removal of the solvent wherein the solvent comprises one or more of methanol, methylene dichloride, tetrahydrofuran, or a mixture thereof.

10. The process according to claim 9, wherein the solvent is removed using a rotational distillation device selected from a rotovapor, spray drying, agitated thin film drying (ATFD), and freeze drying (lyophilization).

11. A process for the preparation of an amorphous form of linagliptin according to claim 1, the process comprising:
(a) suspending linagliptin in one or more solvents and removing the solvent to obtain a residue;
(b) adding an anti-solvent to the residue; and
(c) obtaining the amorphous form of linagliptin wherein the solvent comprises one or more of methanol, acetone, methylene dichloride, or a mixture thereof, and the anti-solvent is methyl tert-butyl ether.

12. A process for the preparation of an amorphous form of linagliptin according to claim 2, the process comprising:
(a) reacting (R)-tert-butyl 1-(7-(but-2-ynyl)-3-methyl-1-((4-methylquinazolin-2-yl)methyl)-2,6-dioxo-2,3,6,7-tetrahydro-1H-purin-8-yl)piperidin-3-ylcarbamate of Formula (2)

(2)

with an acid in a first solvent to obtain a reaction mixture;
(b) basifying the reaction mixture with an aqueous base thereby separating an organic layer;
(c) acidifying the organic layer with an acid followed by treatment with a base to adjust the basic pH;
(d) removing the first solvent to obtain a residue;
(e) treating the residue with a second solvent followed by its partial removal to obtain linagliptin;
(f) dissolving linagliptin in a solvent selected from methanol, methylene dichloride, tetrahydrofuran or mixture thereof and removing the solvent to obtain a second residue; and
(g) obtaining an amorphous form of linagliptin by treating the second residue with an anti-solvent.

13. The process according to claim 12 wherein the first solvent in step (a) comprises one or more of water, methanol, ethanol, isopropanol, ethyl acetate, isopropyl acetate, methylene dichloride, dimethylformamide, dimethylsulfoxide, and tetrahydrofuran.

14. The process according to claim 12 wherein the acid in step (a) comprises one or more of hydrochloric acid, sulfuric acid, acetic acid, triflouroacetic acid, formic acid, and hydrobromic acid.

15. The process according to claim 12, wherein the base in step (c) comprises sodium carbonate, potassium carbonate, sodium bicarbonate, potassium bicarbonate, sodium hydroxide, potassium hydroxide, and lithium hydroxide.

16. The process according to claim 12, wherein the acid in step (c) comprises one or more of oxalic acid, tartaric acid, succinic acid, acetic acid, citric acid, phthalic acid, methane sulfonic acid, toluene sulfonic acid, and mandelic acid or an aqueous solution thereof.

17. The process according to claim 12, wherein the second solvent comprises one or more of methanol, ethanol, isopropanol, acetone, methyl ethyl ketone, methyl isobutyl ketone, toluene, xylene, hexane, heptane, cyclohexane, diisopropyl ether, diethyl ether, and methyl tert-butyl ether.

18. The process according to claim 12, wherein the anti-solvent is methyl tert-butyl ether.

19. A process for the preparation of an amorphous form of linagliptin, substantially free from one or more of residual solvents, according to claim 3 the process comprising:
(a) providing linagliptin having less than 10% of one or more of residual solvents;
(b) triturating the linagliptin in methyl tert-butyl ether, or contacting the linagliptin with humid air in a fluidized bed drier, or drying the linagliptin under reduced pressure of less than about 30 mmHg at less than 60° C.;
(c) optionally micronizing the linagliptin; and
(d) drying the product obtained in step (b) or step (c) to obtain amorphous form of linagliptin substantially free from one or more residual solvents.

20. A process for preparing the amorphous form of linagliptin according to claim 1, having particle size in terms of $D_{95}$ about 100 μm or less, the process comprising the steps of:

(a) milling an amorphous linagliptin,
(b) slurrying the milled linagliptin in one or more organic solvents to form a solution; and
(c) obtaining the amorphous form of linagliptin having particle size in terms of $D_{95}$ of about 100 μm or less by the removal of the solvent, wherein the milling in step (a) is carried out with a feeding pressure of about 3 Kg and a grinding pressure of about 4 Kg.

21. The process according to claim 20 wherein the solvent comprises one or more of acetone, water, N-methylpyrrolidone, dimethylformamide, dimethylacetamide, chlorobenzene, dimethylsulfoxide, dimethylcarbonate, methanol, ethanol, acetonitrile, ethyl acetate, isopropyl acetate, cellosolve, and methyl tert-butyl ether.

22. A method for treating diabetes or type-I diabetes or type-II diabetes or prediabetes or reduction of glucose tolerance comprising administering a therapeutically effective amount of an amorphous form of linagliptin according to claim 2, together with one or more pharmaceutically acceptable carriers, excipients or diluents.

\* \* \* \* \*